United States Patent [19]
Olson et al.

[11] Patent Number: 5,792,190
[45] Date of Patent: Aug. 11, 1998

[54] AUTOMATED EXTERNAL DEFIBRILLATOR OPERATOR INTERFACE

[75] Inventors: Kenneth F. Olson, Minneapolis; Byron L. Gilman, Plymouth; Katherine H. Anderson, Golden Valley; Karl J. F. Kroll, Maple Grove, all of Minn.

[73] Assignee: SurVivaLink Corporation, Minneapolis, Minn.

[21] Appl. No.: 971,762

[22] Filed: Nov. 17, 1997

Related U.S. Application Data

[63] Continuation of Ser. No. 509,990, Aug. 1, 1995, abandoned.
[51] Int. Cl.$^6$ ............................................. A61N 1/39
[52] U.S. Cl. ................................................. 607/5
[58] Field of Search .................................. 607/5, 6, 8

[56] References Cited

U.S. PATENT DOCUMENTS

| | | | |
|---|---|---|---|
| 3,857,398 | 12/1974 | Rubin | 128/419 D |
| 3,886,950 | 6/1975 | Ukkestad et al. | 128/419 D |
| 4,494,552 | 1/1985 | Heath | 128/696 |
| 4,610,254 | 9/1986 | Morgan et al. | 128/419 D |
| 4,619,265 | 10/1986 | Morgan et al. | 128/419 D |
| 4,785,812 | 11/1988 | Pihl et al. | 607/8 |
| 4,823,796 | 4/1989 | Benson | 128/419 D |
| 5,097,830 | 3/1992 | Eikefjord et al. | 128/419 D |
| 5,402,884 | 4/1995 | Gilman et al. | 206/328 |
| 5,405,361 | 4/1995 | Persson | 607/5 |

FOREIGN PATENT DOCUMENTS

| | | |
|---|---|---|
| 0 487 776 A1 | 11/1990 | European Pat. Off. |
| WO 94/26350 | 11/1994 | WIPO |
| WO 94/27674 | 12/1994 | WIPO |
| WO 95/05215 | 2/1995 | WIPO |

OTHER PUBLICATIONS

"Responder 1500 Defibrillator," Marquette Electronics, undated, 2 pages.
"Lifepak 10," Physio-Control, undated, 2 pages.
"Laerdal's Heartstart 3000 ATS," Laerdal Medical Corporation, 1 page, 1991.

(List continued on next page.)

*Primary Examiner*—William E. Kamm
*Assistant Examiner*—Kennedy J. Schaetzle
*Attorney, Agent, or Firm*—Patterson & Keough, P.A.

[57] ABSTRACT

A portable automated external defibrillator (AED) configured for use with a packaged pair of defibrillator electrodes of the type electrically coupled to one another within the package and having lead wires extending from the package and an electrical connector on the ends of the lead wires. The AED includes a case with an electrode compartment configured to hold the packaged electrodes, and an openable lid for enclosing the compartment. Electrode terminals configured for electrical interconnection to the electrical connector of the electrodes, a speaker and an LED display are positioned within the electrode compartment. An operator-actuated rescue switch and a rescue LED display are positioned on the outside of the case. A high voltage circuit generates defibrillation pulses and applies the pulses to the electrode terminals. The operation of the AED is controlled by a digital control system. Rescue mode operation of the AED is initiated when the lid is opened. The digital control system then generates voice prompts and/or visual displays informing the operator: 1) when the electrodes are not properly connected to the electrode terminals, 2) when to place the electrodes on the patient, 3) when the electrodes are not properly positioned on the patient, 4) when the patient's cardiac rhythm is being analyzed, 5) when an nonshockable rhythm is identified, 6) when the high voltage circuit is being charged, and 7) when a shockable rhythm is identified and the rescue switch can be actuated.

26 Claims, 4 Drawing Sheets

OTHER PUBLICATIONS

"First Medic 510 Defibrillator," SpaceLabs Medical, 1 page, undated.

"First Medic 610 Defibrillator," SpaceLabs Medical, 1 page, undated.

"The Nihon Kohden TEC–7300A Defibrillator," Technical Data, 1 page, undated.

"TEC–7000A Series Portable Defibrillators," 2 pages, undated.

"HP 43110A Defibrillator with EMS Option E01," Hewlett Packard, 2 pages, undated.

"HP 43100A Defibrillator with EMS Option E01," Hewlett Packard, 2 pages, undated.

"CodeMaster XL," CodeMaster XE, CodeMaster XL+, HP CodeMaster XL + Defibrillator, 3 pages, undated.

"Porta–Fib LPD I and LPD IIS," Telecare, 1 page, undated.

"HP 43130A", 1 page, undated.

"Cardiac emergencies, PPG Hellige Defiport SCP 912," 1 page, undated.

"Zoll Cardiac Resuscitation," Zoll Medical Corporation, 1 page, undated.

"Zoll PD 1400 Pacemaker/Defibrillator," Zoll Medical Corporation, 1 page, undated.

"First Medic 610 Semi-Automatic Defibrillator," 1 page, undated.

"Lifepak 11 diagnostic cardiac monitor," Physio Control, 1 page, undated.

"Lifepak 10 defibrillator/monitor/pacemaker," Physio Control, 1 page, undated.

"Lifepak 250 automatic advisory defibrillator," Physio Control, 1 page, undated.

"Proof that good things come in small packages," 1 page, undated.

"The Tough Team," SpaceLabs, Inc., Feb. 1992, 9 pages.

"Responder 1200 Defibrillator," Marquette Electronics, 1991, 6 pages.

"Laerdal Heartstart 1000s," Laerdal, 9 pages, undated.

"Lifepak 300 automatic advisory defibrillator without printer," Physio Control, 1 page, undated.

W. A. Tacker Jr., *Defibrillation of the Heart*, 1994 pp. 196–222 (Ch 10).

"Zoll PD 1400 Pacemaker/Defibrillator," Zoll Medical Corporation, 1 page, Physio Control LIFEPAK 300 Operating Instructions 40 pp.

Laerdal Medical, Laerdal Heartstart 2000 Operating Instructions 17 pp.

"First Medic 510 Semi-Automatic Defibrillator," 4 pp.

"First Medic 610 Semi-Automatic Defibrillator," 2 pp.

"First Medic Data Manager V. 2.0", 1 pp.

"Space Labs Medical Operations Manual," 90526 First Medic 610 Semi-automatic Defibrillator, 37 pp.

SurVivaLink Corporation Progress Report, Nov. 1, 1993.

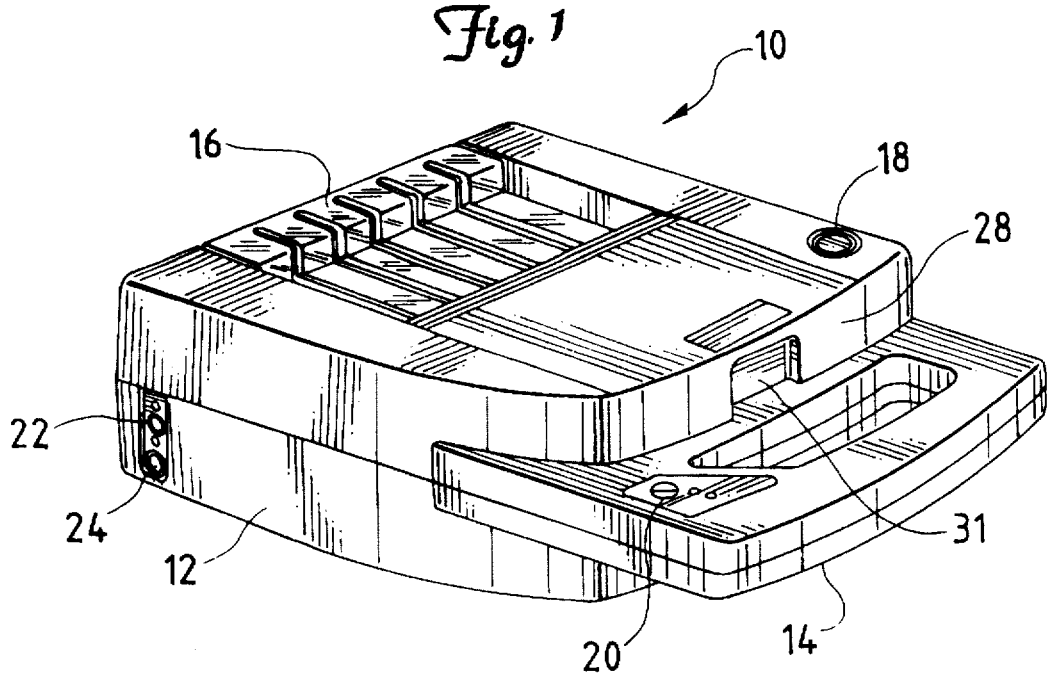
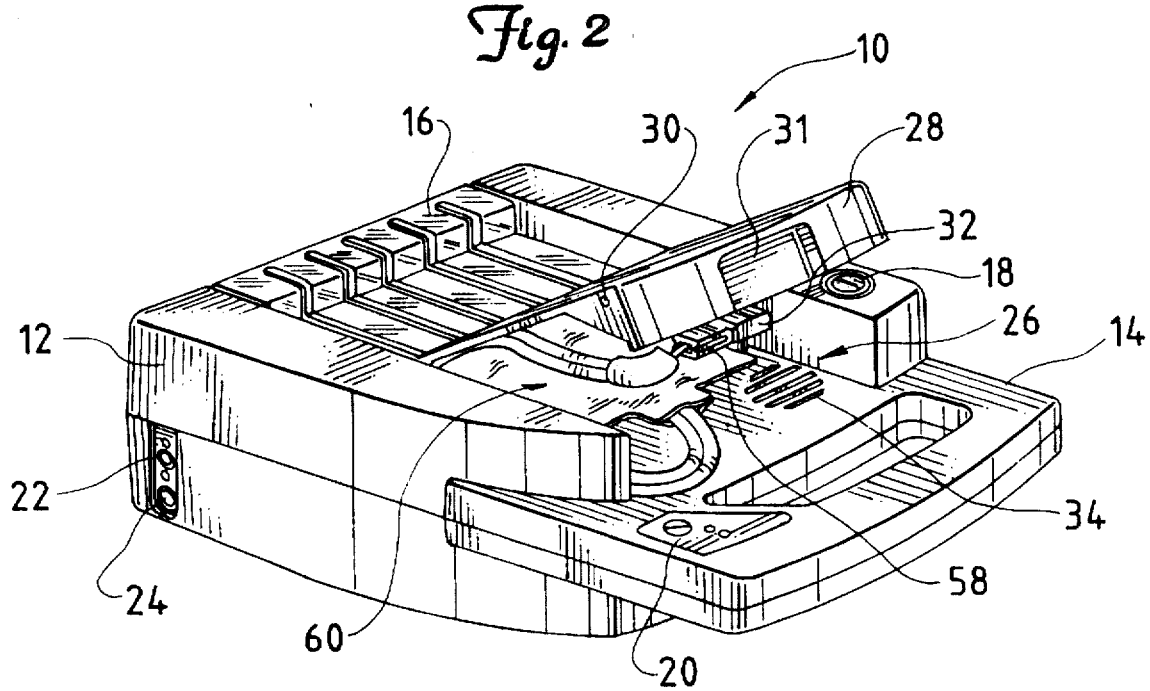

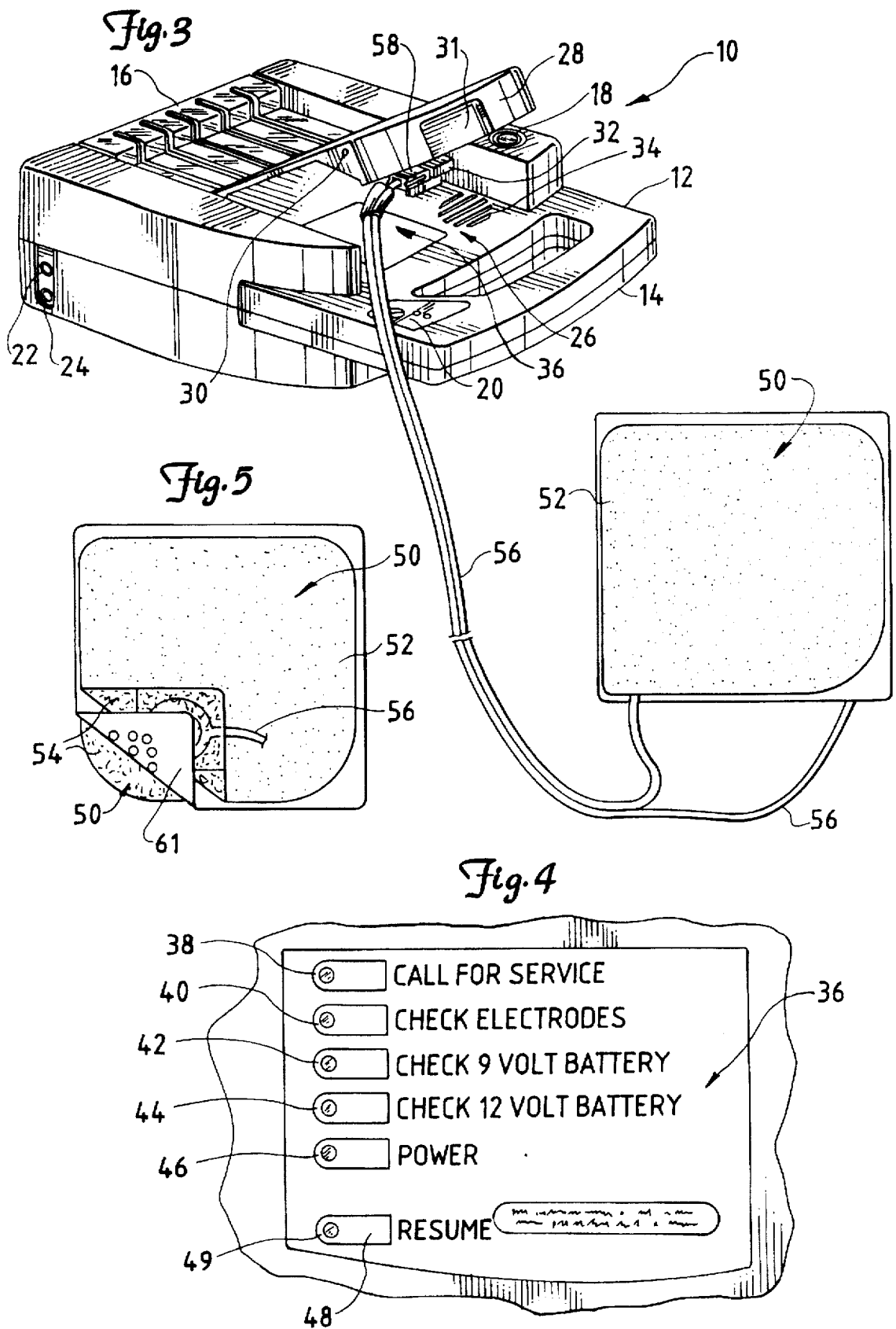

AUTOMATED EXTERNAL DEFIBRILLATOR OPERATOR INTERFACE

This is a Continuation of application Ser. No. 08/509,990, filed Aug. 1, 1995, now abandoned.

BACKGROUND OF THE INVENTION

1. Field of the Invention

The present invention relates generally to automated external defibrillators. In particular, the present invention is an operator interface for an automated external defibrillator.

2. Description of the Related Art

Automated external defibrillators or AEDs are commonly used by police officers, paramedics and other first-responder emergency medical technicians to resuscitate cardiac arrest patients. Generally, to perform a rescue using an AED the medical technician will interconnect a pair of defibrillation electrodes to the defibrillator, position the electrodes on the patient's chest and operate the defibrillator through its operator interface. AED operator interfaces typically include a number of switches that must be actuated to turn the defibrillator on and to initiate the application of defibrillation pulses. Visual displays, audible indicators and voice prompts which indicate the operational status of the defibrillator and instruct the technician on the use of the device are also sometimes included in AED operator interfaces.

AEDs are used in high-stress emergency situations. Time is also of the essence since studies have also shown that the chances of successfully resuscitating a patient decrease approximately ten percent per minute following cardiac arrest. There is, therefore, a continuing need for improved AEDs and associated operator interfaces that are relatively easy-to-use and capable of providing high-quality defibrillation rescues.

SUMMARY OF THE INVENTION

The present invention is an improved automated external defibrillator (AED). One embodiment of the defibrillator includes a case having an electrode compartment configured to hold a pair of defibrillator electrodes, and an openable lid for enclosing the compartment. A lid switch on the case senses when the lid is opened. Electrode terminals in the electrode compartment are configured for electrical interconnection to the defibrillator electrodes. A battery compartment and battery terminals in the case are configured for holding and electrical interconnection to one or more batteries. A high voltage circuit for generating defibrillation pulses is coupled to the battery and electrode terminals. An operator-actuated rescue switch and a rescue indicator are also located on the case. A digital control system is coupled to the lid switch, electrode terminals, high voltage circuit, rescue switch and rescue indicator. The digital control system includes rescue mode initiating means, rhythm analyzing means, rescue indicator actuating means and pulse initiating means. The rescue mode initiating means initiates rescue mode operation of the defibrillator when the lid is opened. Signals present on the electrode terminals are analyzed by the rhythm analyzing means to identify a shockable cardiac rhythm. When a shockable rhythm is identified, the rescue indicator is activated by the rescue indicator actuating means. The pulse initiating means actuates the high voltage circuit and causes the generation of defibrillation pulses when a shockable rhythm is identified and the rescue switch is actuated. The rescue indicator can include both an audible voice prompt and a visual display.

Another embodiment of the invention is configured for use with a pair of packaged electrodes electrically connected to one another within the package, and further includes a place electrodes indicator, a check electrodes indicator and an impedance measuring circuit. The place electrodes indicator includes an audible voice prompt. The check electrodes indicator includes both an audible voice prompt and a visual display. The impedance measuring circuit is coupled between the electrode terminals and the digital control system, and measures the impedance between the electrode terminals. The digital control system of this embodiment includes place electrodes indicator actuating means, electrode connection checking means and electrode application checking means. The place electrodes indicator actuating means actuates the place electrodes indicator after the lid is opened and before analyzing signals present on the electrode terminals. The electrode connection checking means identifies improper electrode connections to the electrode terminals as a function of the measured impedance between the electrode terminals, and actuates the check electrode indicator when improper electrode connections are identified. The electrode application checking means identifies improper electrode placement on a patient as a function of the measured impedance between the electrode terminals, and actuates the check electrodes indicator when improper electrode placement is identified.

Yet another embodiment of the defibrillator includes an audible voice prompt analyzing rhythm indicator, an audible voice prompt charging indicator and an audible voice prompt nonshockable rhythm indicator. The digital control system of this embodiment further includes rhythm indicator actuating means, charging indicator actuating means and nonshockable rhythm indicator actuating means. The rhythm indicator actuating means actuates the analyzing rhythm indicator when analyzing signals on the electrode terminals to identify a shockable rhythm. The charging indicator actuating means actuates the charging indicator when the high voltage circuit is charging and before the rescue indicator is actuated. The nonshockable rhythm indicator actuating means actuates the nonshockable rhythm indicator when a nonshockable rhythm is identified by the rhythm analyzing means.

BRIEF DESCRIPTION OF THE DRAWINGS

FIG. 1 is a perspective view of an automated external defibrillator (AED) in accordance with the present invention, with the electrode compartment lid closed.

FIG. 2 is a perspective view of the AED shown in FIG. 1, with the electrode compartment lid opened and the packaged electrodes positioned therein.

FIG. 3 is a perspective view of the AED shown in FIG. 2, with the electrodes removed from the electrode compartment and the package.

FIG. 4 is a detailed view of the diagnostic display panel in the electrode compartment.

FIG. 5 is a detailed view of the unpackaged electrodes positioned on the release liner.

DETAILED DESCRIPTION OF THE PREFERRED EMBODIMENTS

Figure 6:
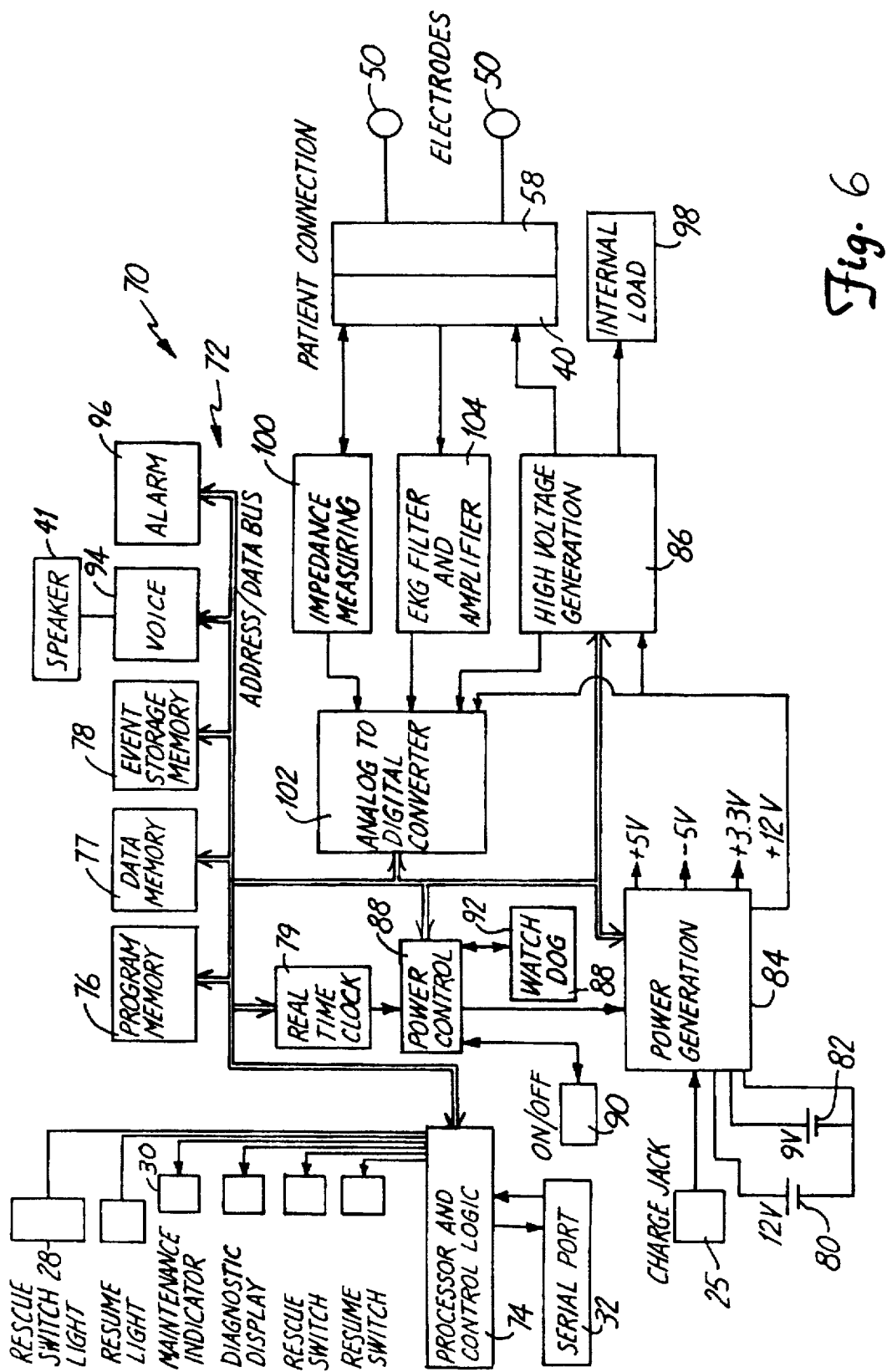
FIG. 6 is a block diagram of the electrical system of the AED shown in FIG. 1.

A semi-automatic, automated external defibrillator (AED) 10 in accordance with the present invention is illustrated generally in FIGS. 1–3. As shown, defibrillator 10 includes a plastic case 12 with a carrying handle 14 on the top portion. A battery compartment (not visible) in the bottom portion of the defibrillator 10 is enclosed by a semitransparent battery cover 16. An illuminatable rescue switch 18, visual maintenance indicator 20, data communication port 22 and charging port 24 are located on the outside of case 12 for easy access by an operator.

Figure 7:
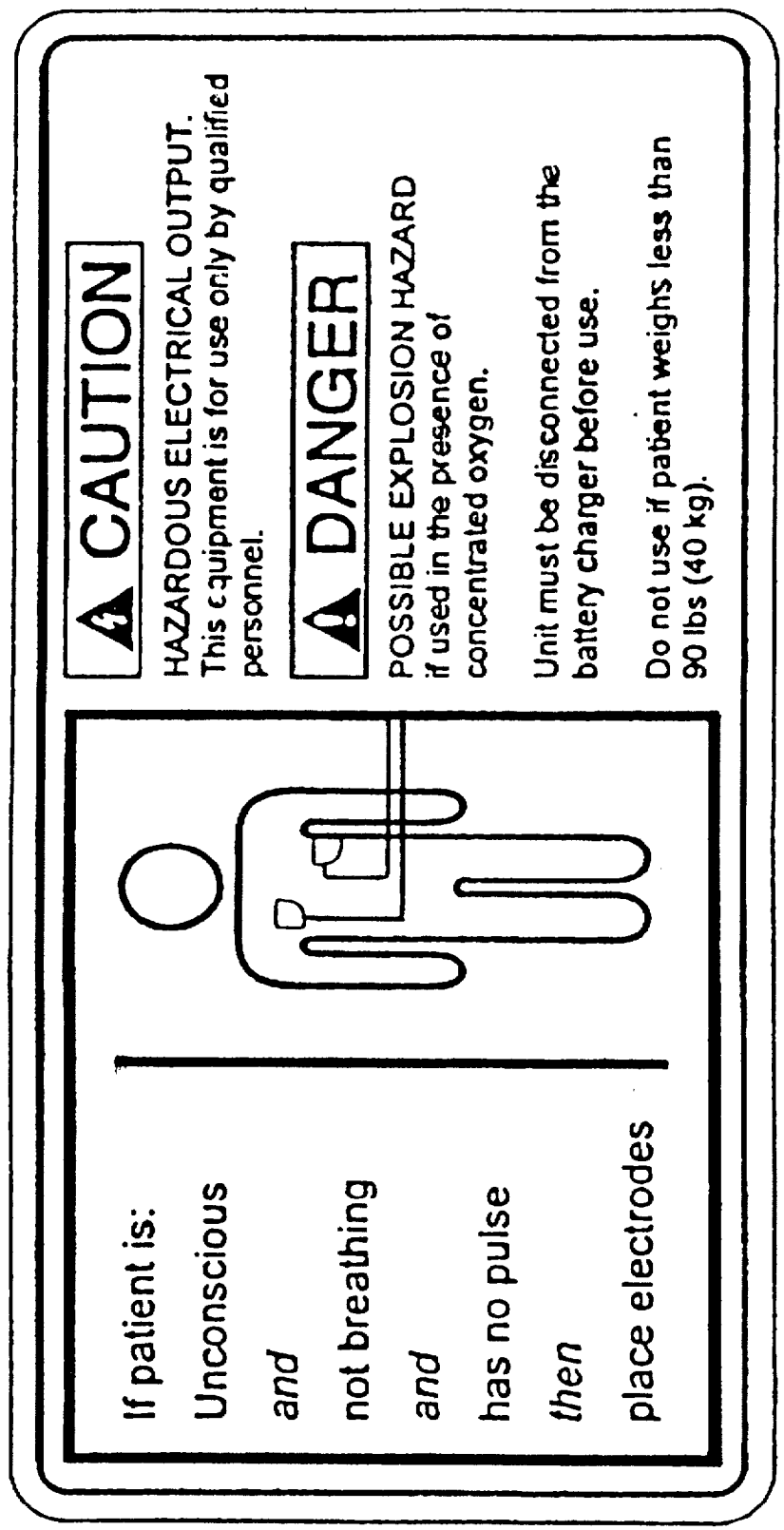
FIG. 7 is an illustration of the instruction and safety label on the inside surface of the electrode compartment lid.

Case 12 also includes an electrode compartment 26 between handle 14 and battery cover 16. The electrode compartment 26 is enclosed by lid 28 which is mounted to the case 12 by hinges (not visible). A friction-type releasable latch including pins 30 holds lid 28 closed when defibrillator 10 is not in use. The finger-receiving recess 31 in the lid 28 is grasped to open the lid and access the electrode compartment 26. An electrode connector 32, speaker 34 and diagnostic display panel 36 are located on case 12 within the electrode compartment 26. As shown in FIG. 4, diagnostic display panel 36 includes visual "Call for Service" indicator light 38, "Check Electrode" indicator light 40, "Check 9 Volt Battery" indicator light 42, "Check 12 Volt Battery" indicator light 44 and "Power" indicator light 46. Resume switch 48 and resume indicator light 49 are also located on diagnostic panel 36. An instruction and safety label such as that shown in FIG. 7 is located on the inside surface of electrode compartment lid 28.

A pair of defibrillator electrodes 50 which can be used with defibrillator 10 are shown in FIGS. 3 and 5. Electrodes 50 each include a flexible polymer backing layer 52 and a patient-engaging layer 54 of conductive adhesive which overlays the backing layer. A current-dispersing flexible conductive sheet (not visible) is located between the backing layer 52 and patient-engaging layer 54. Insulated lead wires 56 extend from each electrode 50, and have a first end connected to the conductive sheet and a second end connected to connector 58. Connector 58 is configured to releasably mate with the electrode connector 32 in electrode compartment 26. Electrodes 50 are sealed within a polymer or polymer-metal laminate package 60 such as that shown in FIG. 2. Lead wires 56 and connector 58 extend from package 60. The layers 54 of electrodes 50 are affixed in a face-to-face orientation to opposite sides of a release liner 61 within package 60. The release liner 61 is perforated with a number of apertures, so the electrodes 50 are electrically coupled to one another within the package 60. A relatively low resistance electrical circuit is thereby established between the ends of the lead wires 56 at connector 58. As shown in FIG. 2, electrode package 60 is positioned within electrode compartment 26, and connector 58 plugged into the connector 32 in the compartment, to maintain defibrillator 10 in a ready-to-use state. Packaged electrodes 50 having the above-described characteristics are disclosed in the Gilman et al. U.S. Pat. No. 5,402,884, and are commercially available from Survivalink of Minnetonka, Minn.

FIG. 6 is a block diagram of the electrical system 70 of defibrillator 10. The overall operation of defibrillator 10 is controlled by a digital microprocessor-based control system 72 which includes a processor 74 interfaced to program memory 76, data memory 77, event memory 78 and real time clock 79. The operating program executed by processor 74 is stored in program memory 76. Data memory 77 is used by processor 74 as a scratch pad memory during the execution of the operating program. Electrical power is provided by a rechargeable twelve volt lead-acid cartridge battery 80 and a nine volt battery 82 which are removably positioned within the battery compartment and connected to power generation circuit 84. During normal operation, power generation circuit 84 generates regulated ±5 V, 3.3 V and 12 V (actually about 13.3 V) supplies with the power provided by the twelve volt battery 80. Nine volt battery 82 functions as a back-up battery to power components of electrical system 70 during the execution of self-tests and to activate maintenance indicators and alarms (as described below) if the twelve volt battery 80 is low on charge. Although not separately shown in FIG. 5, power generation circuit 84 includes voltage level sensing circuits which are coupled to processor 74. The voltage level sensing circuits provide low battery level signals to processor 74 whenever the voltage levels of batteries 80 or 82 are less than predetermined values such as 12.3 V and 8 V, respectively.

The ±5 V supply is used to power the control system 72 and most other electrical components of electrical system 70. The 3.3 V supply is coupled to nonvolatile event memory 78 in which, as is described in greater detail below, data representative of the patient's cardiac rhythm and the rescue mode operation of defibrillator 10 are stored. A high voltage generation circuit 86 is connected to receive the 12 V supply. Charging port 24 is coupled to power generation circuit 84, enabling twelve volt battery 80 to be connected to a twelve volt vehicle battery (not shown) or a 120 VAC charger (also not shown) and recharged while mounted within the defibrillator 12. Alternatively battery 80 can be removed from defibrillator 10 and charged in a stand-alone charger (not shown). Defibrillator 10 cannot be operated when a charger is connected to charge port 24. Circuitry (not separately shown) within power generation circuit 84 senses the interconnection of port 24 to a charger, and provides a charger connected signal to processor 74 when a connected charger is sensed.

Power generation circuit 84 is also connected to power control circuit 88 and processor 74. Power control circuit 88 is connected to lid switch 90, watch dog timer 92, real time clock 79 and processor 74. Lid switch 90 is a magnetic reed relay switch in one embodiment, and provides signals to processor 74 indicating whether lid 28 is open or closed. Data communication port 22 is coupled to processor 74 for two-way serial data transfer using an RS-232 protocol. Rescue switch 18, maintenance indicator 20, rescue switch light 19, resume switch 48, indicator lights 38, 40, 42, 44, 46 and 49 of diagnostic display panel 36, voice circuit 94 and piezoelectric audible alarm 96 are also connected to processor 74. Voice circuit 94 is connected to the speaker 34. In response to voice prompt control signals from processor 74, circuit 94 and speaker 34 generate the audible voice prompts described below.

High voltage generation circuit 86 is also connected to and controlled by processor 74. Circuits such as 86 are generally known, and disclosed, for example, in the commonly assigned Persson et al. U.S. Pat. No. 5,405,361, which is hereby incorporated by reference. In response to charge control signals provided by the processor 74, high voltage generation circuit 86 is operated in a charge mode during which one set of semiconductor switches (not separately shown) cause a plurality of capacitors (also not shown), to be charged in parallel to the 12 V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 32 which is connected to the high voltage generation circuit 86. Under certain circumstances described below, processor 74 causes high voltage generation circuit 86 to be discharged through an internal resistive load 98 rather than connector 32.

Impedance measuring circuit 100 is connected to electrode connector 32 and real time clock 79, and is interfaced to processor 74 through analog-to-digital (A/D) converter 102. The impedance measuring circuit 100 receives a clock signal having a predetermined magnitude from clock 79, and applies the signal to electrodes 50 through connector 32. The magnitude of the clock signal received back from the electrodes 50 through connector 32 is monitored by impedance measuring circuit 100. An impedance signal representative of the impedance present across electrode connector 32 is then generated by circuit 100 as a function of the ratio of the magnitudes of the applied and received clock signals (i.e., the attenuation of the applied signal). For example, if the electrodes 50 within package 60 are operational and the connector 58 is properly connected to connector 32 on defibrillator 10, a relatively low resistance (e.g., less than about ten ohms) should be present across the connector 32. If the conductive adhesive on the electrodes 50 is dried out, the connector 58 is not properly connected to connector 32, or the electrodes are not properly positioned on the patient, a relatively high resistance (e.g., greater than about one hundred ohms) will be present across the connector 32. The resistance across connector 32 will be between about fifty and eighty ohms when fresh electrodes 50 are properly positioned on the patient with good electrical contacts. The impedance signal representative of the impedance measured by circuit 100 is digitized by A/D converter 102 and provided to processor 74.

Defibrillator 10 also includes electrocardiogram (EKG) filter and amplifier 104 which is connected between electrode connector 32 and A/D converter 102. The EKG or cardiac rhythm of the patient is processed by filter and amplifier 104 in a conventional manner, and digitized by A/D converter 102 before being coupled to processor 74.

The rescue mode operation of defibrillator 10 is initiated when an operator opens lid 28 to access the electrode package 60. The opening of the lid 28 is detected by lid switch 90, which effectively functions as an on/off switch. In response to this action, power control circuit 88 activates power generation circuit 84 and initiates rescue mode operation of processor 74. Processor 74 then begins its rescue mode operation by switching maintenance indicator 20 to a maintenance required state (e.g., a yellow visual display in one embodiment), flashing rescue switch light 19 and the indicator lights on diagnostic display panel 36, and performing a lid opened self-test. Processor 74 also initiates the generation of an audible voice prompt "To attempt a rescue, disconnect charger." if a charger is connected to charge port 24 when lid 28 is opened.

During the lid opened self-test, processor 74 checks: 1) the charge state of batteries 80 and 82, 2) the interconnection and operability of electrodes 50, 3) the state of event memory 78, 4) the functionality of real time clock 79, and 5) the functionality of A/D converter 102. The charge states of batteries 80 and 82 are checked by monitoring the voltage level signals provided by power generation circuit 84. If batteries 80 and/or 82 are determined to have a low charge, lights 44 and/or 42, respectively, on diagnostic display panel 36 are illuminated by processor 74. The interconnection and operability of the electrodes 50 is checked by monitoring the impedance signals provided by impedance measuring circuit 100. If the package 60 of electrodes 50 is missing or unplugged from connector 32, or if the electrodes are damaged (e.g., dried out), processor 74 will illuminate the indicator light 40 on diagnostic display panel 36. As described in greater detail below, data representative of the operation of defibrillator 10 during a rescue and the patient's cardiac rhythm are stored in event memory 78. The data can be subsequently retrieved from event memory 78 through communications port 22, and the memory cleared. During the lid opened self-test, processor 74 accesses the event memory 78 to determine whether data from a previous rescue is still stored in the memory. If so, processor 74 causes light 49 on diagnostic panel 36 to be illuminated, and initiates the generation of a "Press resume button to clear memory and continue." voice prompt. If resume switch 18 is pressed by the operator following the activation of these indicators, processor 74 clears event memory 78 and proceeds with its rescue mode operation. The functionality of real time clock 79 and A/D converter 102 are checked by monitoring the outputs of these circuit elements for expected signals. Diagnostic display panel light 38 is illuminated by processor 74 if faults are identified in either of clock 79 or converter 102.

If the lid opened self-test is successfully completed, processor 74 switches maintenance indicator 20 to an operational state (e.g., a black color in one embodiment), and initiates the generation of an audible "Place electrodes." voice prompt. In response to this voice prompt, and following the instructions on the inside of lid 28, the operator should remove electrode package 60 from compartment 26, open the package, peel electrodes 50 from the release liner 61 and place the electrodes on the patient's chest. While this action is being performed, processor 74 monitors the impedance signals received through A/D converter 102 to determine whether the impedance across the electrodes indicates that they have been properly positioned on the patient. If the correct impedance is not measured, processor 74 initiates the generation of a "Check electrodes." voice prompt.

After detecting an impedance indicating the proper placement of electrodes 50, and without further action by the operator (i.e., automatically) , processor 74 begins a first analyze sequence by initiating the generation of a "Do not touch patient. Analyzing rhythm." voice prompt, and analyzing the patient's cardiac rhythm. In one embodiment, processor 74 collects and analyzes a nine second segment of the patient's cardiac rhythm. The cardiac rhythm analysis program executed by processor 74 is stored in program memory 76. Algorithms of the type implemented by the rhythm analysis program are generally known and disclosed, for example, in the W. A. Tacker Jr. book *Defibrillation of the Heart*, 1994. If the processor 74 determines that the patient has a nonshockable cardiac rhythm that is not susceptible to treatment by defibrillation pulses (e.g., no pulse rather than a fibrillating rhythm), it initiates the generation of a "Check pulse. If no pulse, give CPR." voice prompt. One minute after this voice prompt, processor 74 repeats the initiation of the "Do not touch patient. Analyzing rhythm." voice prompt and the associated cardiac rhythm analysis.

When a shockable cardiac rhythm is detected, processor 74 begins a first charge sequence by initiating the generation of a "Charging." voice prompt, and causes high voltage generation circuit 86 to operate in the charge mode. When the high voltage generation circuit 86 is charged, processor 74 begins a first shock sequence by initiating the generation of a "Stand clear. Push flashing button to rescue." voice prompt, and the flashing illumination of rescue switch light 19. The operator actuation of rescue switch 18 will then cause processor 74 to operate high voltage generation circuit 86 in the discharge mode, and results in the application of a defibrillation pulse to the patient to complete the first series of analyze/charge/shock sequences. In one embodiment, the first defibrillation pulse delivered by defibrillator 10 has an energy content of about two hundred joules.

Following the first series of analyze/charge/shock sequences, processor 74 times out a short pause of about five seconds to allow the heart to reestablish its cardiac rhythm before beginning a second series of analyze/charge/shock sequences. The second series of analyze/charge/shock sequences is identical to the first series described above, except the energy content of the defibrillation pulse can be about two hundred joules or three hundred joules. If the second series of analyze/charge/shock sequences ends with the delivery of a defibrillation pulse, processor 74 again times out a short pause of about five second before beginning a third analyze/charge/shock sequence. The third series is also identical to the first series, but processor 74 controls the high voltage generation circuit 86 in such a manner as to cause the defibrillation pulse delivered upon the actuation of the rescue switch 18 to have an energy content of about three hundred and sixty joules.

Following the delivery of a defibrillation pulse at the end of the third series of analyze/charge/shock sequences, or after identifying a nonshockable cardiac rhythm, processor 74 initiates the generation of a "Check Pulse. If no pulse, give CPR." voice prompt. Processor 74 then times a one minute CPR period to complete a first set of three series of analyze/charge/shock sequences. Rescue mode operation then continues with additional sets of three series of analyze/charge/shock sequences of the type described above (all with three hundred and sixty joule pulses). Processor 74 ends rescue mode operation of defibrillator 10 when a total of nine series of analyze/charge/shock sequences have been performed, or lid 28 is closed.

Throughout the analyze, charge and shock sequences, processor 74 monitors the impedance present across connector 32 to determine whether electrodes 50 remain properly positioned on the patient. If the monitored impedance is out of range (e.g., too high if the electrodes have come off the patient, or too low if shorted), processor 74 initiates the generation of a "Check Electrodes." voice prompt, and causes high voltage generation circuit 86 to discharge any charge that may be present through internal load 98. Rescue mode operation will resume when processor 74 determines that the electrodes have been properly repositioned on the patient.

Processor 74 initiates and performs a lid closed self-test when lid 28 is closed following rescue mode operation of the defibrillator 10. During the lid closed self-test processor 74 performs a comprehensive check of the status and functionality of defibrillator 10, including: 1) the state of event memory 78, 2) the functionality of real time clock 79, 3) the functionality of A/D converter 102, 4) the functionality of program memory 76, data memory 77 and event memory 78, 5) the charge state of batteries 80 and 82, and 6) the interconnection and operability of electrodes 50. The state of event memory 78, the state of batteries 80 and 82, the interconnection and operability of electrodes 50, and the functionality of clock 79 and A/D converter 102 are checked in a manner identical to that described above with reference to the lid opened self-test. Conventional memory test routines are implemented to check the functionality of program memory 76, data memory 77 and event memory 78. Light 38 on diagnostic display panel 36 is illuminated (when lid 28 is subsequently opened), and maintenance indicator 20 is switched to its maintenance required state by processor 74 if faults are identified during the lid closed self-test. No audible alarms are actuated if faults are identified in the charge state of batteries 80 or 82 or the interconnection or functionality of electrodes 50 during the lid closed self test. However, alarm 96 is actuated by processor 74 if other faults are identified during the lid opened self test.

A daily self-test is initiated and performed by processor 74 at a predetermined time each day (i.e., every twenty-four hours). During the daily self-test processor 74 performs all the component check operations described above that are performed during the lid opened and lid closed self-tests. In addition to illuminating the appropriate lights on diagnostic display panel 36, processor 74 switches maintenance indicator 20 to its maintenance required state and activates alarm 96 if faults are identified during the daily self-test.

Processor 74 also initiates and performs a weekly self-test at a predetermined time one day each week. During the weekly self-test processor 74 performs all the component check operations described above that are performed during the daily self-test. In addition, processor 74 causes high voltage generation circuit 86 to sequentially operate in its charge and discharge modes, with the charge being dumped to the internal load 98. While the high voltage generation circuit 86 is operating in the charge mode, processor 74 monitors the time required to charge the capacitors and the capacitor voltage. A fault is identified if either is out of nominal conditions. Maintenance indicator 20 and alarm 96 are actuated in the manner described above if any faults are identified during the weekly self-test.

Watch dog timer 92 is set to time watch dog time-out periods of about thirty hours (i.e., a period greater than the twenty-four hour periods between daily self-tests), and is reset by processor 74 at the beginning of each daily self-test and each time lid 26 is opened. In the event control system 70 malfunctions and watch dog timer 92 times out, power control circuit 88 causes processor 74 to switch maintenance indicator 20 to the maintenance required state and to actuate alarm 96 to alert an operator to the fact that defibrillator 10 requires maintenance.

Data representative of the operation of defibrillator 10 and the monitored cardiac rhythm of the patient are stored in event memory 78 during rescue mode operation. Stored data representative of the operation of defibrillator 10 includes the real time of the occurrence of each of the following events: 1) the placement of electrodes 50 on the patient, 2) the initiation of the cardiac rhythm analysis voice prompt, 3) the initiation of the charging voice prompt, 4) the completion of the charge mode operation of high voltage generation circuit 86 , and 5) the actuation of rescue switch 18. The actual time base of the patient's cardiac rhythm is also stored in memory 78. Following a rescue, the stored data can be retrieved from event memory 78 through the use of a personal computer (PC) (not shown) interfaced to communications port 22. Real time clock 79 can also be set through the use of a PC interfaced to communications port 22.

Defibrillator 10 offers considerable advantages. In particular, the device is relatively easy to use. The lid-actuated on-off switch, voice prompts, "one button" rescue operation and other aspects of the operator interface help enable high-quality defibrillation rescues. The wide range of self-tests and diagnostic displays enable operators to conveniently and accurately assess the operational status of the defibrillator.

Although the present invention has been described with reference to preferred embodiments, those skilled in the art will recognized that changes can be made in form and detail without departing from the spirit and scope of the invention.

What is claimed is:

1. An automated external defibrillator, comprising:
   a pair of defibrillator electrodes having a stored disposition and an operating disposition, the electrodes being disposed in an electrically conductive relationship in said stored disposition;
   a case including an electrode compartment and an openable lid for enclosing the compartment, the compartment configured to hold the pair of defibrillator electrodes;
   a lid switch for sensing when the lid is opened;
   electrode terminals in the electrode compartment, the electrode terminals configured for electrical interconnection to the defibrillator electrodes;
   a battery compartment and battery terminals in the case, the battery compartment and terminals and configured for holding and electrical interconnection to one or more batteries;
   a high voltage circuit coupled to the battery terminals and the electrode terminals, for generating defibrillation pulses and applying the pulses to the electrode terminals;
   an operator-actuated rescue switch on the case;
   a rescue indicator on the case; and
   a digital control system coupled to the lid switch, electrode terminals, high voltage circuit, rescue switch and rescue indicator, including:
      rescue mode initiating means for initiating rescue operation of the defibrillator when the lid is opened;
      rhythm analyzing means for analyzing signals present on the electrode terminals to identify a shockable cardiac rhythm;
      rescue indicator actuating means for activating the rescue indicator when a shockable rhythm is identified; and
      pulse initiating means for actuating the high voltage circuit and causing the generation of defibrillation pulses when a shockable rhythm is identified and the rescue switch is actuated;
      resume indicator actuating means for actuating the resume indicator if rescue data is stored in the digital control system when the lid is opened; and
      memory clearing means for clearing the rescue data from the digital control system when the resume button is actuated.

2. The defibrillator of claim 1 wherein the rescue indicator includes a speaker communicatively coupled to the digital control system for providing an audible voice prompt.

3. The defibrillator of claim 1 wherein the rescue indicator includes a visual display.

4. The defibrillator of claim 1 wherein:
   the defibrillator further includes:
      an impedance measuring circuit coupled between the electrode terminals and the digital control system, for measuring the impedance between the electrode terminals; and
      a check electrodes indicator; and
   the digital control system further includes electrode application checking means for identifying improper electrode placement on a patient and disconnection of at least one of the pair of electrodes from the patient as a function of the measured impedance between the electrode terminals, and for actuating the check electrodes indicator when improper electrode placement is identified.

5. The defibrillator of claim 4 wherein:
   the defibrillator further includes an internal load coupled to the high voltage circuit; and
   the electrode application checking means causes the high voltage circuit to dissipate any charge to the internal load when the measured impedance between the electrode terminals indicates an improper electrode placement or electrode disconnect.

6. The defibrillator of claim 4 wherein the check electrode indicator includes a speaker communicatively coupled to the digital control system for providing a voice prompt.

7. The defibrillator of claim 4 wherein the check electrode indicator includes a visual display.

8. The defibrillator of claim 4 wherein:
   the digital control system further includes electrode checking means for identifying improper electrode connections to the electrode terminals and for identifying damaged electrodes as a function of the measured impedance between the electrode terminals, and actuates the check electrode indicator when improper electrode connections are identified.

9. The defibrillator of claim 1 wherein:
   the defibrillator further includes an analyzing rhythm indicator; and
   the digital control system further includes rhythm indicator actuating means for actuating the analyzing rhythm indicator when analyzing signals on the electrode terminals to identify a shockable rhythm.

10. The defibrillator of claim 9 wherein the analyzing rhythm indicator includes a speaker communicatively coupled to the digital control system for providing a voice prompt.

11. The defibrillator of claim 1 wherein:
    the defibrillator further includes a nonshockable rhythm indicator; and
    the digital control system further includes nonshockable indicator means for actuating the nonshockable rhythm indicator when an nonshockable rhythm is identified by the rhythm analyzing means.

12. The defibrillator of claim 11 wherein the nonshockable rhythm indicator includes a speaker communicatively coupled to the digital control system for providing a voice prompt.

13. The defibrillator of claim 1 wherein:
    the defibrillator further includes a data communication port on the case coupled to the digital control system; and
    the digital control system further includes:
       event storage means for storing rescue data representative of the rescue operation of the defibrillator and/or monitored cardiac rhythms; and
       rescue data transfer means for transferring the rescue data to the data communication port.

14. An automated external defibrillator, comprising:
    a case including an electrode compartment and an openable lid for enclosing the compartment, the compartment configured to hold a pair of defibrillator electrodes;
    a lid switch for sensing when the lid is opened;
    electrode terminals in the electrode compartment, the electrode terminals configured for electrical interconnection to the defibrillator electrodes;
    a battery compartment and battery terminals in the case, the battery compartment and terminals being configured for holding an electrical interconnection to one or more batteries;

a high voltage circuit coupled to the battery terminals and the electrode terminals, for generating defibrillation pulses and applying the pulses to the electrode terminals;

an operator-actuated rescue switch on the case;

a rescue indicator on the case;

a digital control system coupled to the lid switch, electrode terminals, high voltage circuit, rescue switch and rescue indicator;

a data communication port on the case coupled to the digital control system;

a resume indicator coupled to the digital control system;

an operator-actuated resume button coupled to the digital control system; and the digital control system including:

rescue mode initiating means for initiating rescue operation of the defibrillator when the lid is opened;

rhythm analyzing means for analyzing signals present on the electrode terminals to identify a shockable cardiac rhythm;

rescue indicator actuating means for activating the rescue indicator when a shockable rhythm is identified;

pulse initiating means for actuating the high voltage circuit and causing the generation of defibrillation pulses when a shockable rhythm is identified and the rescue switch is actuated;

event storage means for storing rescue data representative of the rescue operation of the defibrillator and/or monitored cardiac rhythms;

rescue data transfer means for transferring the rescue data to the data communication port;

resume indicator actuating means for actuating the resume indicator if rescue data is stored in the digital control system when the lid is opened; and memory clearing means for clearing the rescue data from the digital control system when the resume button is actuated.

15. The defibrillator of claim 14 wherein the resume indicator includes a speaker communicatively coupled to the digital control system for providing a voice prompt.

16. The defibrillator of claim 14 wherein the resume indicator includes a visual display.

17. An automated external defibrillator, comprising:

a case including an electrode compartment and an openable lid for enclosing the compartment, the compartment configured to hold a pair of defibrillator electrodes;

electrode terminals on the case configured for electrical interconnection to defibrillator electrodes;

a battery compartment and battery terminals in the case, the battery compartment and terminals configured for holding and for electrical interconnection to one or more batteries;

a high voltage circuit coupled to the battery terminals and the electrode terminals, for generating defibrillation pulses and applying the pulses to the electrode terminals;

an on/off switch on the case;

an operator-actuated rescue switch on the case;

a rescue indicator on the case; and a digital control system coupled to the on/off switch, electrode terminals, high voltage circuit, rescue switch and rescue indicator, including:

rescue mode initiating means for initiating rescue operation of the defibrillator when the on/off switch is actuated;

rhythm analyzing means for analyzing signals present on the electrode terminals to identify a shockable cardiac rhythm after the on/off switch is actuated;

rescue indicator actuating means for activating the rescue indicator when a shockable rhythm is identified;

pulse initiating means for actuating the high voltage circuit and causing the generation of defibrillation pulses when a shockable rhythm is identified and the rescue switch is actuated;

a resume indicator coupled to the digital control system;

an operator-actuated resume button coupled to the digital control system;

resume indicator actuating means for actuating the resume indicator if rescue data is stored in the digital control system when the lid is opened; and memory clearing means for clearing the rescue data from the digital control system when the resume button is actuated.

18. The defibrillator of claim 17 wherein:

the on/off switch includes a lid switch for sensing when the lid is opened; and the rescue mode initiating means is responsive to the lid switch and initiates rescue mode operation of the defibrillator when the lid is opened.

19. The defibrillator of claim 17 wherein:

the defibrillator further includes an impedance measuring circuit coupled to the electrode terminals and the digital control system, for measuring the impedance between the electrode terminals in both the stored disposition and the operating disposition;

the digital control system further includes electrode application checking means for identifying improper electrode placement on a patient as a function of the measured impedance between the electrode terminals when the electrodes are in the operating disposition; and the rhythm analyzing means includes means for automatically initiating the analysis of signals present on the electrode terminals when proper electrode placement is identified by the electrode application checking means.

20. The defibrillator of claim 19 wherein:

the defibrillator further includes a check electrodes indicator; and the electrode application checking means actuates the check electrode indicator when improper electrode placement on the patient or a disconnect of at least on electrode from the patient is identified.

21. The defibrillator of claim 17 wherein:

the defibrillator further includes a place electrodes indicator; and the digital control system further includes a place electrodes indicator actuating means for actuating the place electrodes indicator after the on/off switch is actuated and before analyzing signals present on the electrode terminals.

22. The defibrillator of claim 21 wherein:

the defibrillator further includes an impedance measuring circuit coupled to the electrode terminals and the digital control system, for measuring the impedance between the electrode terminals;

the digital control system further includes electrode application checking means for identifying improper electrode placement on a patient as a function of the measured impedance between the electrode terminals; and the rhythm analyzing means includes means for automatically initiating the analysis of signals present on the electrode terminals when proper electrode placement is identified by the electrode checking means.

23. The defibrillator of claim 22 wherein:

the defibrillator is configured for use with a pair of packaged electrodes electrically coupled to one another within the package; and the digital control system further includes electrode connection checking means for identifying improper electrode connections to the electrode terminals as a function of the measured impedance between the electrode terminals, and actuates the check electrode indicator when improper electrode connections are identified.

24. An automated external defibrillator, comprising:

a pair of defibrillator electrodes having a stored disposition and an operating disposition, the electrodes being disposed in an electrically conductive relationship in said stored disposition;

a case;

electrode terminals on the case configured for electrical interconnection to the defibrillator electrodes;

a battery compartment and battery terminals in the case, the battery compartment and terminals configured for holding and for electrical interconnection to one or more batteries;

a high voltage circuit coupled to the battery terminals and the electrode terminals, for generating defibrillation pulses and applying the pulses to the electrode terminals;

an impedance measuring circuit coupled to the electrode terminals, for measuring the impedance between the electrode terminals;

an on/off switch on the case;

an operator-actuated rescue switch on the case;

a rescue indicator on the case;

a digital control system coupled to the on/off switch, electrode terminals, high voltage circuit, rescue switch, impedance measuring circuit and rescue indicator;

a resume indicator coupled to the digital control system;

an operator-actuated resume button coupled to the digital control system; and the digital control system including:

rescue mode initiating means for initiating rescue operation of the defibrillator when the on/off switch is actuated;

electrode application checking means for identifying improper electrode placement on a patient as a function of the measured impedance between the electrode terminals;

rhythm analyzing means for automatically analyzing signals present on the electrode terminals to identify a shockable cardiac rhythm when proper electrode placement is identified;

rescue indicator actuating means for activating the rescue indicator when a shockable rhythm is identified;

pulse initiating means for actuating the high voltage circuit and causing the generation of defibrillation pulses when a shockable rhythm is identified and the rescue switch is actuated;

resume indicator actuating means for actuating the resume indicator if rescue data is stored in the digital control system when the lid is opened; and memory clearing means for clearing the rescue data from the digital control system when the resume button is actuated.

25. The defibrillator of claim 24 wherein:

the defibrillator further includes a place electrodes indicator; and the digital control system further includes place electrodes indicator actuating means for actuating the place electrodes indicator after the on/off switch is actuated and before analyzing signals present on the electrode terminals.

26. The defibrillator of claim 24 wherein:

the defibrillator further includes a check electrodes indicator; and the electrode application checking means actuates the check electrodes indicator when improper electrode placement is identified.

* * * * *

UNITED STATES PATENT AND TRADEMARK OFFICE
CERTIFICATE OF CORRECTION

PATENT NO. : 5,792,190
DATED : August 11, 1998
INVENTOR(S) : Kenneth F. Olson, Byron L. Gilman, Katherine H. Anderson, Karl J.F. Kroll It is certified that error appears in the above-identified patent and that said Letters Patent is hereby corrected as shown below:

In the Abstract, line 23, please change the word "an" to the word "a".

Column 1, line 46, please change the word "and" to the word "an".

Column 3, line 53, please change the spelling of the word "Survivalink" to "SurVivaLink".

Column 3, line 54, please change "FIG. 6" to "FIG. 5".

Column 5, lines 53-56, please delete the bold highlighting from the numerals "1)", "2)", "3)", "4)", and "5)".

Column 6, line 37, please delete the space between "(i.e., automatically)" and the ",".

Column 7, line 14, please change the word "second" to "seconds".

Column 8, line 66, please change the word "recognized" to "recognize".

UNITED STATES PATENT AND TRADEMARK OFFICE
CERTIFICATE OF CORRECTION

PATENT NO. : 5,792,190
DATED : August 11, 1998
INVENTOR(S) : Kenneth Fl.Olson, Byron L. Gilman, Katherine H. Anderson, Karl J.F. Kroll It is certified that error appears in the above-identified patent and that said Letters Patent is hereby corrected as shown below:

Column 9, line 16, please delete the word "and".

Column 9, line 17, please change the word "and" to the word "an".

Column 9, line 20, please delete the comma following the word "terminals".

Column 9, line 24, please delete the word "and".

Column 12, line 51, at the end of line 51 please change the word "on" to the word "one".

Column 13, line 34, please delete the comma following the word "terminals".

Signed and Sealed this

Eighth Day of December, 1998

Attest:

BRUCE LEHMAN

*Attesting Officer*    *Commissioner of Patents and Trademarks*